United States Patent
Micinski

(10) Patent No.: US 7,416,430 B2
(45) Date of Patent: Aug. 26, 2008

(54) CONTACT CONNECTOR ASSEMBLY FOR A SENSOR-DISPENSING INSTRUMENT

(75) Inventor: Russell J. Micinski, South Bend, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 11/660,243

(22) PCT Filed: Aug. 19, 2005

(86) PCT No.: PCT/US2005/029694

§ 371 (c)(1),
(2), (4) Date: Feb. 13, 2007

(87) PCT Pub. No.: WO2006/023810

PCT Pub. Date: Mar. 2, 2006

(65) Prior Publication Data

US 2008/0083773 A1    Apr. 10, 2008

Related U.S. Application Data

(60) Provisional application No. 60/603,008, filed on Aug. 20, 2004.

(51) Int. Cl.
H01R 11/22 (2006.01)
(52) U.S. Cl. .................. 439/267; 439/260; 439/725; 439/909
(58) Field of Classification Search ......... 439/266–267, 439/259–260, 635, 725, 909, 660; 600/365; 221/69
See application file for complete search history.

(56) References Cited

U.S. PATENT DOCUMENTS

| | | | | |
|---|---|---|---|---|
| 4,270,826 A | * | 6/1981 | Narozny | 439/260 |
| 4,761,143 A | * | 8/1988 | Owens et al. | 439/372 |
| 4,801,272 A | * | 1/1989 | Kanazawa et al. | 439/153 |
| 4,934,947 A | | 6/1990 | Brummans et al. | 439/77 |
| 5,489,414 A | | 2/1996 | Schreiber et al. | 422/64 |
| 5,575,403 A | | 11/1996 | Charlton et al. | 221/31 |
| 5,620,579 A | | 4/1997 | Genshaw et al. | 204/402 |

(Continued)

FOREIGN PATENT DOCUMENTS

| | | |
|---|---|---|
| CA | 2 423 837 A1 | 9/2007 |
| EP | 1 118 856 A1 | 7/2001 |
| EP | 1 152 239 A1 | 11/2001 |
| EP | 1 288 659 A2 | 3/2003 |
| EP | 1 284 161 B1 | 2/2006 |
| WO | WO 01/71328 A1 | 9/2001 |
| WO | WO 03/042691 | 5/2003 |
| WO | WO 2004/063747 A1 | 7/2004 |

*Primary Examiner*—Michael C Zarroli
(74) *Attorney, Agent, or Firm*—Nixon Peabody LLP

(57) ABSTRACT

A contact connector assembly, which is adapted to be used in a sensor-dispensing instrument that contains electrochemical test sensors, comprises at least four electrical contacts, a housing connector, a base connector and a moveable mechanism. The housing connector forms a housing opening that is adapted to receive the at least four electrical contacts. The base connector is coupled to the housing connector and forms a sensor-receiving opening. The base or housing connector is adapted to move between first and second positions. The moveable mechanism is coupled to the housing or base connector. The moveable mechanism is adapted to move the base or housing connector between the first and second positions. The housing and base connectors are adapted to be coupled in a first position such that they are adapted to hold one of the test sensors. The housing and base connectors are adapted to be coupled in a second position such that they allow the test sensor to be removed therefrom.

27 Claims, 10 Drawing Sheets

U.S. PATENT DOCUMENTS

| | | | |
|---|---|---|---|
| 5,630,986 A | 5/1997 | Charlton et al. | 422/64 |
| 5,645,798 A | 7/1997 | Schreiber et al. | 422/58 |
| 5,653,863 A | 8/1997 | Genshaw et al. | 205/777.5 |
| 5,722,845 A * | 3/1998 | Debortoli et al. | 439/267 |
| 5,723,284 A | 3/1998 | Ye | 435/4 |
| 5,733,151 A * | 3/1998 | Edsall et al. | 439/729 |
| 5,738,244 A | 4/1998 | Charlton et al. | 221/26 |
| 5,856,195 A | 1/1999 | Charlton et al. | 436/50 |
| 5,944,562 A | 8/1999 | Christensson | 439/729 |
| 6,152,754 A * | 11/2000 | Gerhardt et al. | 439/325 |
| 6,246,966 B1 | 6/2001 | Perry | 702/91 |
| 6,623,312 B2 * | 9/2003 | Merry et al. | 439/729 |
| 6,671,534 B2 * | 12/2003 | Putz | 600/378 |
| 6,722,906 B2 * | 4/2004 | Tsing | 439/260 |
| 2003/0031591 A1 | 2/2003 | Whitson et al. | 422/50 |
| 2003/0032190 A1 | 2/2003 | Brown et al. | 436/46 |
| 2003/0089730 A1 | 5/2003 | May et al. | 221/232 |
| 2003/0111357 A1 | 6/2003 | Black | 205/775 |
| 2003/0203498 A1 | 10/2003 | Neel et al. | 436/95 |
| 2004/0048394 A1 | 3/2004 | Kirchhevel | 436/183 |
| 2004/0069793 A1 | 4/2004 | Brown et al. | 221/30 |
| 2004/0118704 A1 | 6/2004 | Wang et al. | 205/792 |

* cited by examiner

CONTACT CONNECTOR ASSEMBLY FOR A SENSOR-DISPENSING INSTRUMENT

CROSS-REFERENCE TO RELATED APPLICATION

This application claims priority to U.S. Provisional Application No. 60/603,008, filed on Aug. 20, 2004.

FIELD OF THE INVENTION

The present invention generally relates to a contact connector assembly for a sensor-dispensing instrument and, more particularly, to a contact connector assembly that is adapted to be used to determine at least one analyte concentration in fluid such as, for example, blood glucose.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. While the remainder of the disclosure herein will be directed towards a contact connector assembly to assist in determining glucose, it is to be understood that it may be used for determining other analytes on selection of an appropriate enzyme.

The results of such tests can be used to determine what, if any, insulin or other medication needs to be administered. In one type of blood glucose testing system, test sensors are used to test a fluid such as a sample of blood.

A test sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested is supplied to contact areas located near the rear or contact end of the sensor.

It would be desirable to have a contact connector assembly that would enable the sensor-dispensing instrument to be a simpler and more reliable mechanism.

SUMMARY OF THE INVENTION

According to one embodiment, a contact connector assembly is adapted to be used in a sensor-dispensing instrument that contains a plurality of electrochemical test sensors. The contact connector assembly comprises at least four electrical contacts, a housing connector, a base connector, and a moveable mechanism. The housing connector forms at least one housing opening. The at least one housing opening is adapted to receive the at least four electrical contacts. The base connector is coupled to the housing connector so as to form a sensor-receiving opening adapted to receive one of the plurality of test sensors. At least one of the base connector and the housing connector is adapted to move between a first position and a second position. The moveable mechanism is coupled to at least one of the housing connector and the base connector. The moveable mechanism is adapted to move at least one of the base connector or the housing connector between the first position and the second position. The housing connector and the base connector are adapted to be coupled in a first position such they are adapted to hold one of the plurality of test sensors. The housing connector and the base connector are adapted to be coupled in a second position such that they allow the test sensor to be removed therefrom.

According to one embodiment, a sensor-dispensing instrument is adapted to determine an analyte concentration. The sensor-dispensing instrument comprises a plurality of electrochemical test sensors, a cartridge, and a contact connector assembly. The cartridge contains the plurality of electrochemical test sensors. The contact connector assembly includes at least four electrical contacts, a housing connector that forms at least one housing opening, a base connector being coupled to the housing connector so as to form a sensor-receiving opening adapted to receive one of the plurality of test sensors, and a moveable mechanism coupled to at least one of the housing connector and the base connector. The at least one housing opening is adapted to receive the at least four electrical contacts. At least one of base connector and the housing connector is adapted to move between a first position and a second position. The moveable mechanism is adapted to move at least one of the base connector and the housing connector between the first position and the second position. The housing connector and the base connector are adapted to be coupled in a first position such they are adapted to hold one of the plurality of test sensors and the one of the plurality of test sensors is adapted to contact the at least four electrical contacts to assist in determining the analyte concentration. The housing connector and the base connector are adapted to be coupled in a second position such that they allow the test sensor to be removed therefrom.

According to one method, a sensor-dispensing instrument is used to determine an analyte concentration. A sensor-dispensing instrument is provided that includes a plurality of electrochemical test sensors, a cartridge containing the plurality of electrochemical test sensors, and a contact connector assembly. The contact connector assembly includes at least four electrical contacts, a housing connector that forms at least one housing opening, a base connector being coupled to the housing connector so as to form a sensor-receiving opening adapted to receive one of the plurality of test sensors, and a moveable mechanism coupled to at least one of the housing connector and the base connector. The at least one housing opening is adapted to receive the at least four electrical contacts. At least one of the base connector and the housing connector is placed in a first position. One of the plurality of test sensors is repositioned from the cartridge to the sensor-receiving opening such that the one of the plurality of test sensors contacts the at least four electrical contacts to assist in determining the analyte concentration. At least one of the base connector and the housing connector is moved to a second position from the first position via the moveable mechanism. A fluid is placed with at least one analyte on the one of the plurality of test sensors. The concentration of the at least one analyte is determined.

BRIEF DESCRIPTION OF THE DRAWINGS

FIG. 2b is a front view of a sensor-dispensing instrument according to one embodiment that is adapted to receive the cartridge of FIG. 2a;

FIG. 6b is a cross-sectional view taken generally along line 6b-6b of FIG. 6a;

Figure 1:
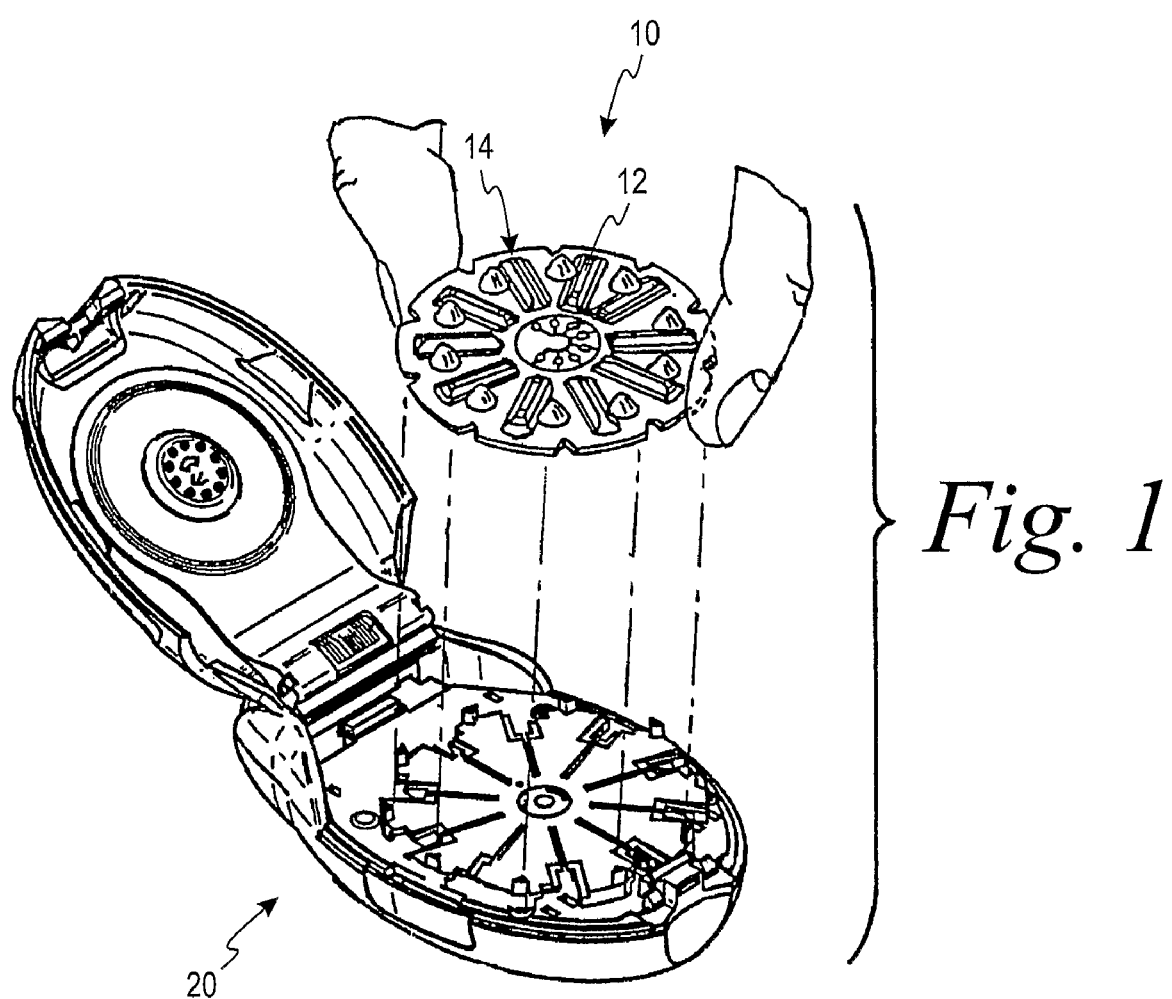
FIG. 1 is a perspective view of a sensor-dispensing instrument in the open position showing a sensor pack being inserted according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE ILLUSTRATED EMBODIMENTS

The present invention is directed to a contact connector assembly to be used in a sensor-dispensing instrument that contains a plurality of electrochemical test sensors. The electrochemical test sensors are used to determine concentrations of at least one analyte in a fluid. Analytes that may be determined using the contact connector assembly of the present invention include glucose, lipid profiles (e.g., cholesterol, triglycerides, LDL and HDL), microalbumin, hemoglobin $A_1C$, fructose, lactate, or bilirubin. The present invention is not limited, however, to determining these specific analytes and it is contemplated that other analyte concentrations may be determined. The analytes may be in, for example, a whole blood sample, a blood serum sample, a blood plasma sample, or other body fluids like ISF (interstitial fluid) and urine.

The plurality of test sensors is typically stored in a disposable cartridge. For example, the plurality of test sensors may be stored in a sensor pack where the test sensors are individually packaged in sensor cavities (e.g., a blister-type pack). An example of a disposable cartridge 10 being placed in a sensor-dispensing instrument 20 is depicted in FIG. 1. The disposable cartridge 10 is an example of a blister-type pack. The cartridge 10 includes a plurality of test sensors 12 that is individually stored in a respective one of sensor cavities 14. It is contemplated that other sensor packs that individually hold the sensors may be used. The disposable cartridge 10 of FIG. 1 is further described at U.S. Publication No. 2003/0032190 that published on Feb. 13, 2003 and is entitled "Mechanical Mechanism for a Blood Glucose Sensor-Dispensing Instrument."

Figure 2A:
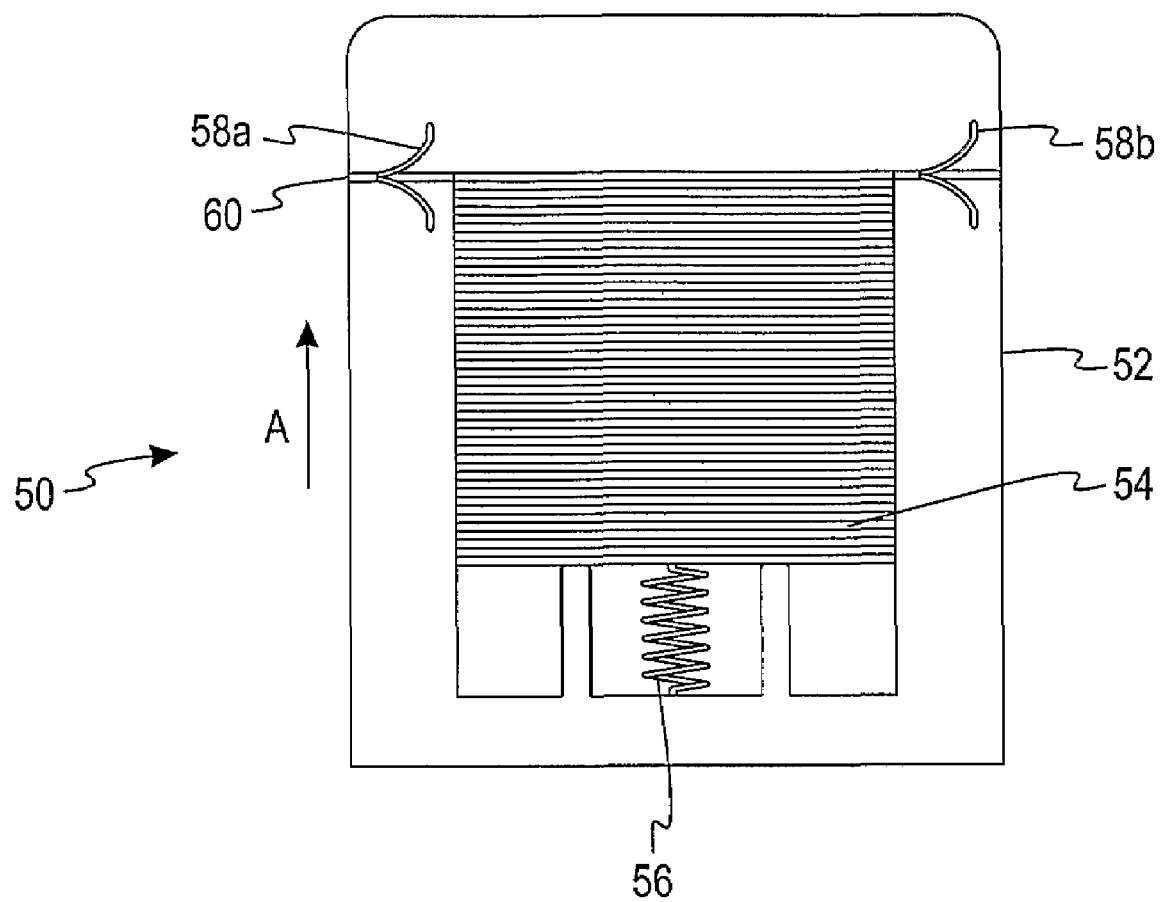
FIG. 2a is a front view of a disposable cartridge with a plurality of stacked test sensors according to one embodiment.
Figure 2B:
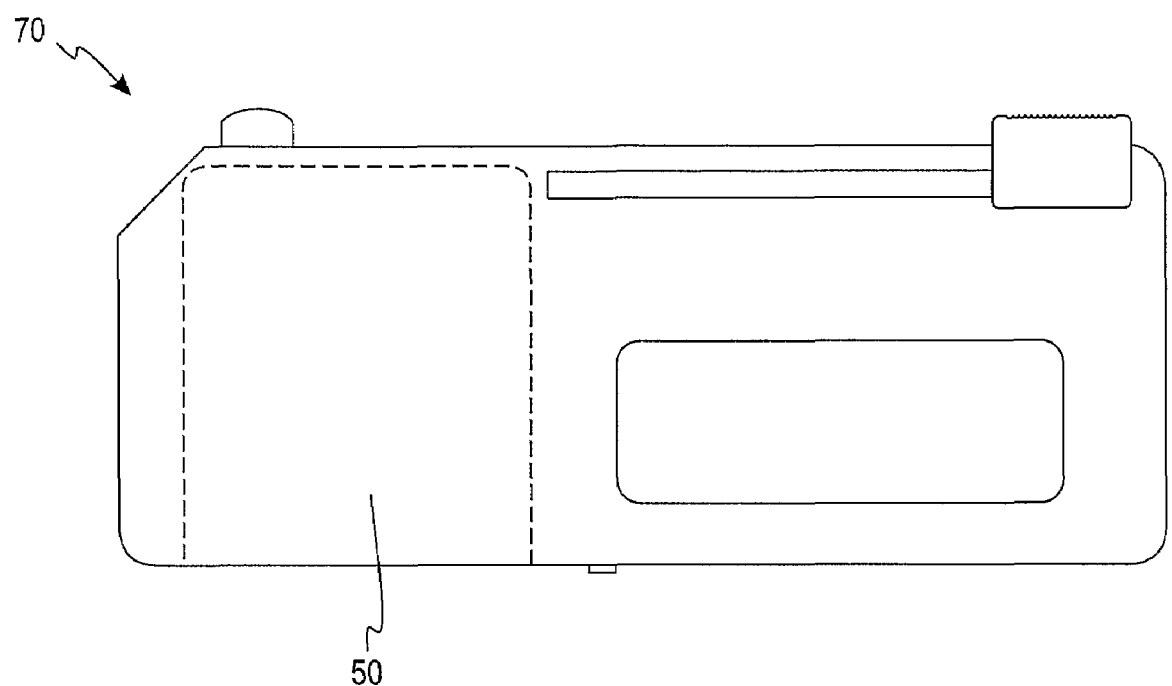

The plurality of test sensors may be stacked in a disposable cartridge such as shown in FIG. 2a. Referring to FIG. 2a, a disposable cartridge 50 includes a housing 52 and a plurality of stacked test sensors 54 that are moved in the direction of arrow A via a spring 56. The cartridge 50 also includes a plurality of seals 58a,b that protects the stacked test sensors 54 from humidity. The test sensors 54, one at a time, exit the cartridge 50, via opening 60. The disposable cartridge 50 may be stored in a sensor-dispensing instrument 70 of FIG. 2b. It is contemplated that other cartridges besides cartridges 10, 50 may be used.

The cartridges 10, 50 of FIGS. 1 and 2a may vary in the number of test sensors that are included so as to address the needs of different users. Typically, the cartridges contain from about 10 to about 50 sensors and, more specifically, contain from about 25 to about 40 sensors. Because of limited shelf-and use-life of the test sensors, it is envisioned that a user who tests infrequently would likely desire a cartridge having less test sensors as opposed to a user who tests more frequently.

The test sensors to be used in the cartridges are typically provided with a capillary channel that extends from the front or testing end of the sensors to biosensing or reagent material disposed in the sensor. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that an electrical signal indicative of the analyte (e.g., glucose) level in the fluid being tested is supplied and subsequently transmitted to an electrical assembly.

Reagent material that may be used to determine the glucose concentration include glucose oxidase. It is contemplated that other reagent material may be used to determine the glucose concentration such as glucose dehydrogenase. It is further contemplated that other reagent material may be used to assist in determining glucose such as, for example, pyrrolo-quinoline quinone glucose dehydrogenase and potassium ferricyanide. The selected reagent may influence items such as the amount of fluid needed and the length of time needed to perform the testing to determine the analyte concentration.

Figure 3B:
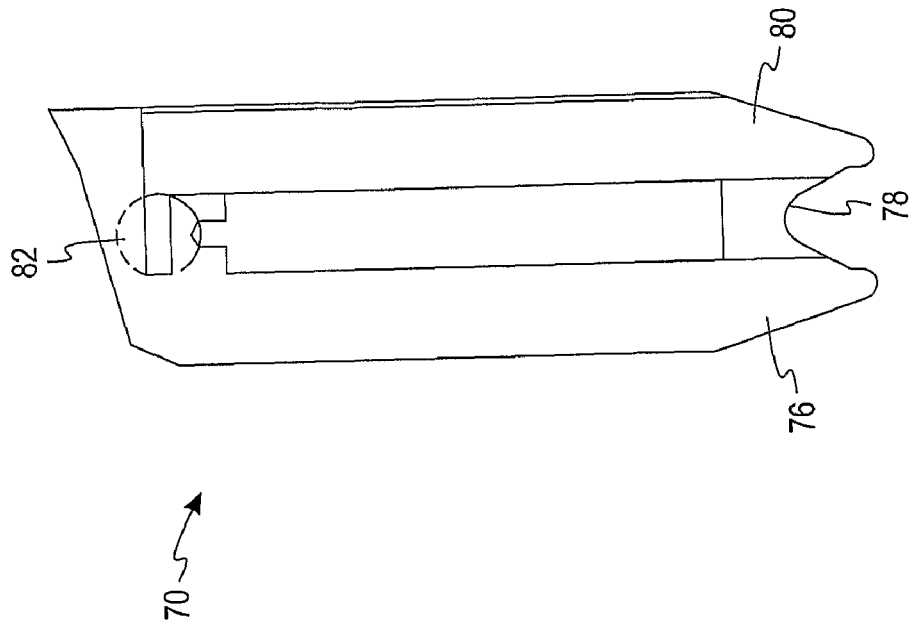
FIG. 3b is the test sensor of FIG. 3a without the lid.
Figure 3A:
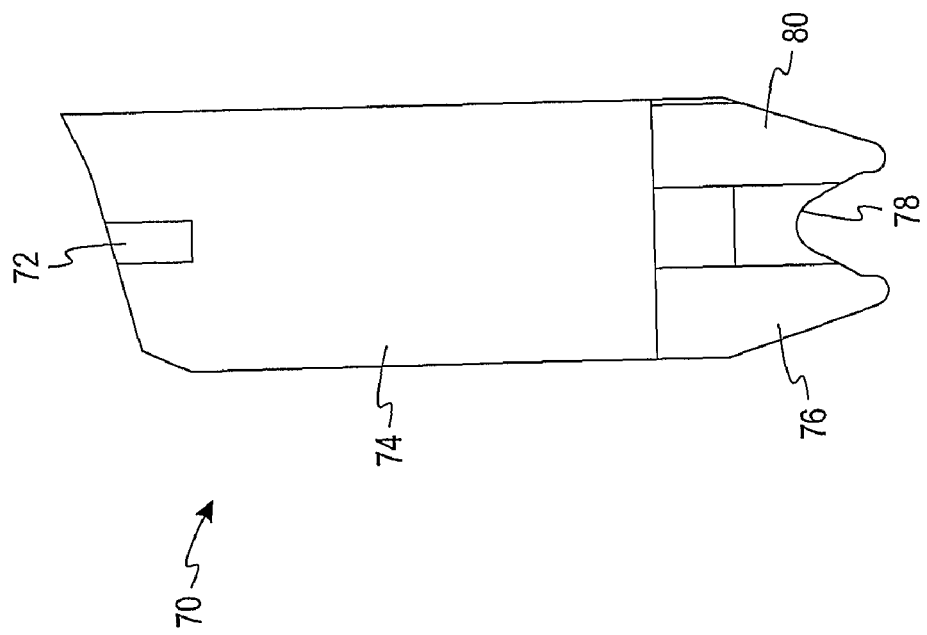
FIG. 3a is a test sensor including a lid according to one embodiment.

One non-limiting example of a test sensor is shown in FIGS. 3a, 3b. FIGS. 3a, 3b depict a test sensor 70 that includes a capillary channel 72, a lid 74, and a plurality of electrodes 76, 78, and 80. The plurality of electrodes includes a counter electrode 76, a detection electrode 78, and a working (measuring) electrode 80. As shown in FIG. 3b, the test sensor 70 includes a fluid-receiving area 82 that contains reagent. The operation of fluid-receiving area with reagent and the electrodes on the test sensors is known to those skilled in the art and will therefore not be described in further detail. Examples of electrochemical test sensors, including their operation, may be found at, for example, U.S. Patent Application published as 2001/0042683 and EP 1152239. It is contemplated that other electrochemical test sensors may be employed.

According to one embodiment, the plurality of test sensors is adapted to auto-calibrate themselves. Having test sensors that auto-calibrate is advantageous because it minimizes the parts needed in the sensor-dispensing instrument. Additionally, having auto-calibration may be desirable because it eliminates the need for a user to enter information about the product lot number of the test sensors so as to perform the correct program associated with the product lot number. It is contemplated, however, that the plurality of test sensors may not have the ability to auto-calibrate themselves.

Figure 4:
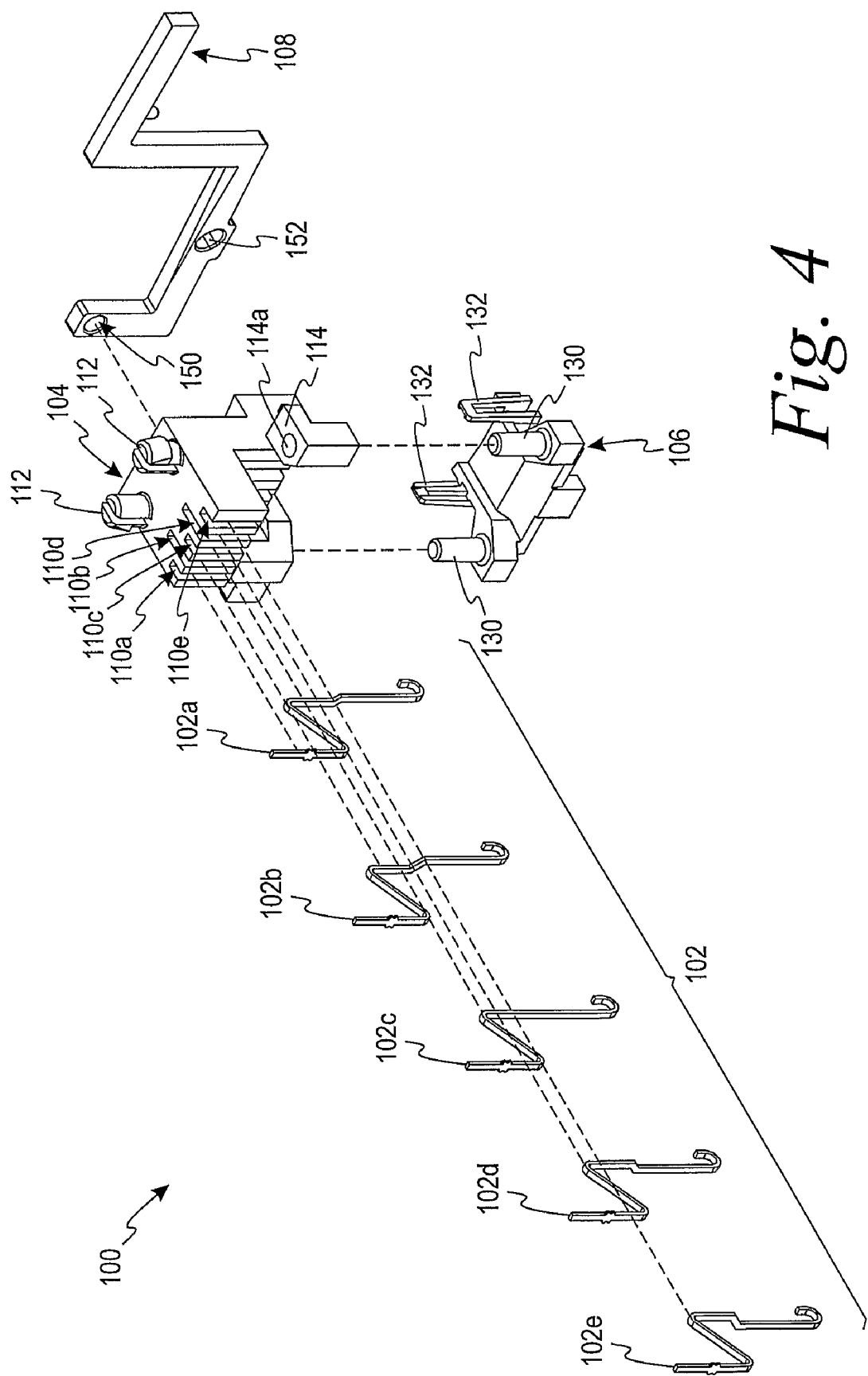
FIG. 4 is an exploded view of a contact connector assembly according to one embodiment of the present invention.

Referring to FIGS. 4 and 5, a contact connector assembly 100 is shown according to one embodiment. The contact connector assembly 100 is adapted to make a connection between the test sensor with reagent and the electronic system of the sensor-dispensing instrument. The software located in the sensor-dispensing instrument uses the electrical signals to output at least one analyte concentration of the fluid (e.g., a blood glucose level). The contact connector assembly 100 comprises at least four electrical contacts 102, a housing connector 104, a base connector 106, and a moveable mechanism 108.

Figure 5A:
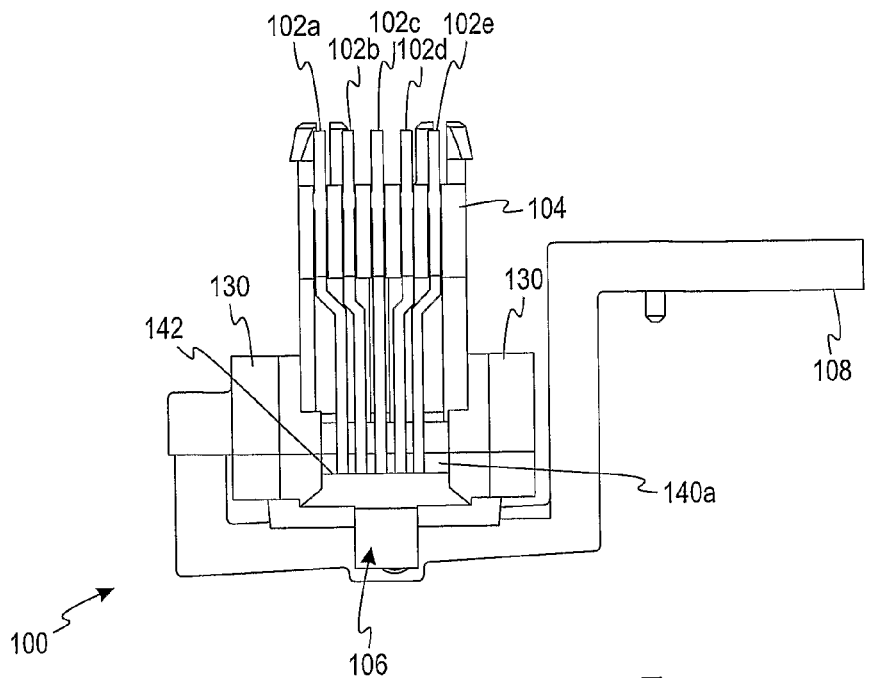
FIG. 5a, 5b are end views of the contact contactor assembly of FIG. 4 in a first position.
Figure 5B:
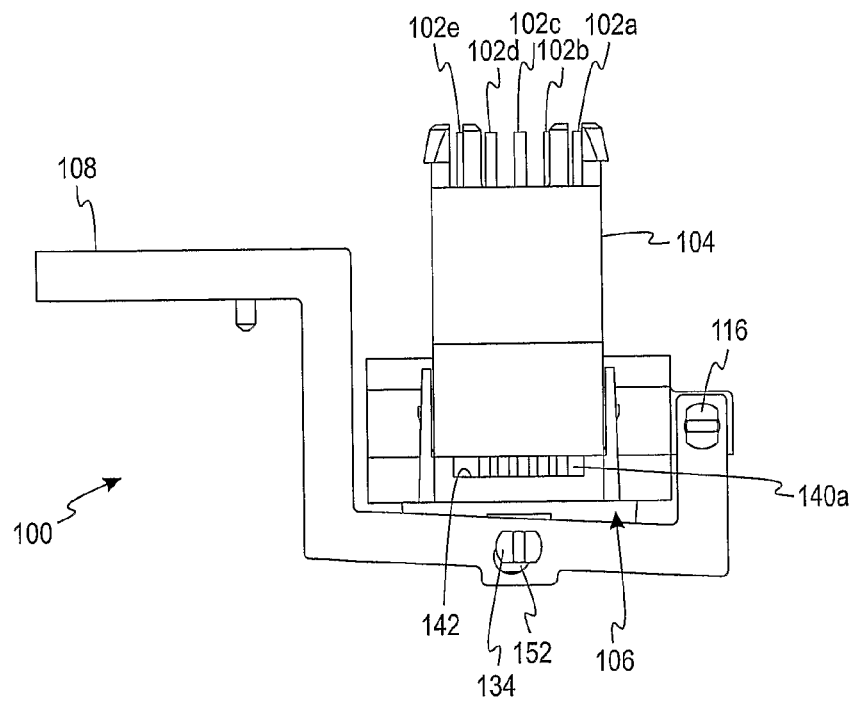
Figure 5C:
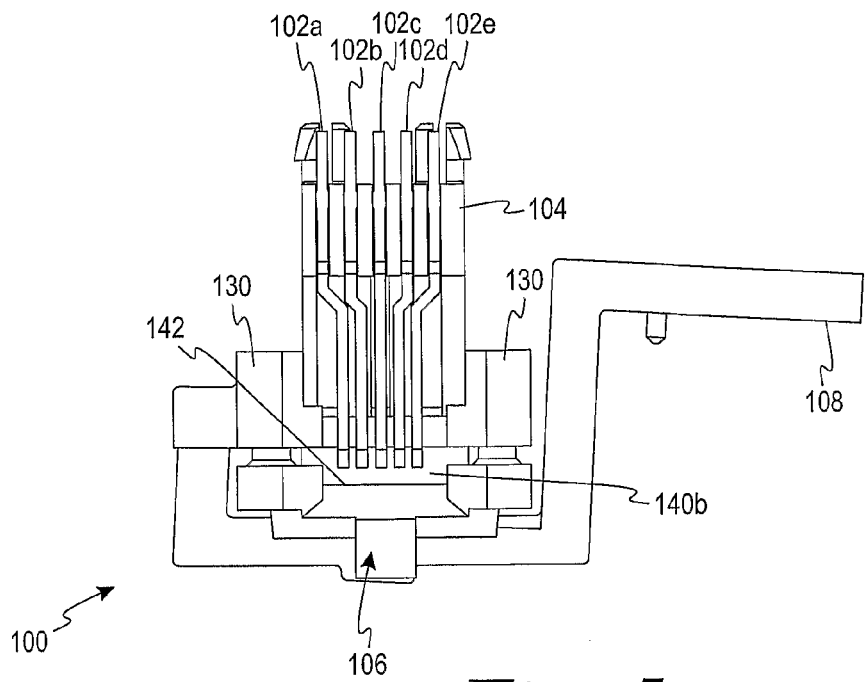
FIG. 5c, 5d are end views of the contact contactor assembly of FIG. 4 in a second position.
Figure 5D:
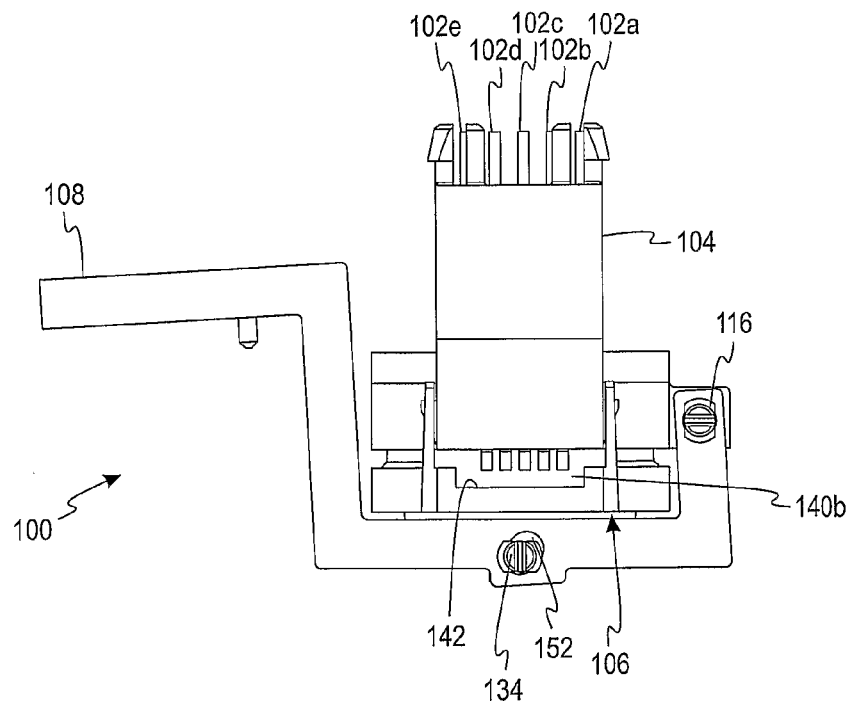

The contact connector assembly 100 of FIGS. 4 and 5 includes exactly five electrical contacts 102*a-e*. It is contemplated that the contact connector assembly may have exactly four electrical contacts or may have six or more electrical contacts. As shown in FIGS. 5 and 6, each of the electrical contacts 102*a-e* is fixed in the housing connector 104. The electrical contacts 102*a-e* are positioned in the housing connector 104 to make contact with a test sensor. Even though the electrical contacts 102*a-e* are fixed in the housing connector 104, the electrical contacts 102*a-e* are allowed to float with respect to the test sensor, which results in a better connection between the electrical contacts and the test sensor. By allowing the electrical sensors 102*a-e* to float, a test sensor when being positioned exerts sufficient upwardly pressure on the electrical sensors 102*a-e*, resulting in the electrical sensors 102*a-e* being moved upward. The amount of potential movement with the electrical contacts 102*a-e* is depicted in FIG. 6*b* with a distance D. To maintain an improved connection between the electrical contacts and the test sensors, the electrical sensors 102*a-e* are desirably formed to maintain downward pressure on the test sensor after the test sensor has been properly positioned with respect to the electrical contacts.

The electrical contacts 102*a-e* may be made of different materials, but are typically made of metal. One example of a material that may be used in forming the electrical contacts is stainless steel. It is contemplated that other materials such as nickel-plated phosphor bronze or nickel-plated beryllium cooper may be used in forming the electrical contacts. The plurality of electrical contacts 102*a-e* may be forming by stamping. Additionally, the plurality of electrical contacts may be shaped differently than depicted in FIG. 4.

In one embodiment, the electrical contacts 102*a-e* are adapted to communicate with an electronic PC board. In such an embodiment, the electrical contacts 102*a-e* may extend through apertures formed in the electronic PC board. To prevent or inhibit losing electrical contact between the electronic PC board and the electrical contacts 102*a-e*, the electrical contacts are typically soldered into place with the electronic PC board.

As shown in FIGS. 4 and 6, the housing connector 104 forms a plurality of housing openings or apertures 110*a-e* that are sized to accept a respective electrical contact 102*a-e*. The housing openings 110*a-e* are shaped as slots in FIGS. 4 and 6. The electrical contacts 102*a-e* are shown in the housing openings 110*a-e* in FIGS. 6*a, c, d*. It is contemplated that the housing connector may have less openings than depicted in FIGS. 4 and 6. For example, the housing connector may have at least one opening that receives the electrical contacts. Such embodiments with fewer openings may be less desirable because of the need to electrically isolate the electrical contacts from each other. It is also contemplated that the housing openings may be shaped different than depicted in FIGS. 4 and 6.

The housing connector 104 also includes a plurality of bosses 112. The bosses 112 are adapted to snap into corresponding apertures formed in the electronic PC board of the sensor-dispensing instrument. It is contemplated that the contact connector assembly may be installed in a different manner to the electronic PC board.

The housing connector 104 further includes a plurality of base-connecting receiving portions 114, an extension 116, and a plurality of generally triangular-shaped plugs 118. Each of the receiving portions 114 forms an aperture 114*a*. As shown in FIGS. 4 and 6, the apertures 114*a* are sized to receive a respective one of a plurality of posts 130 that is formed in the base connector 106. As shown in FIGS. 4, 5*b*, 5*d*, the extension 116 of the housing connector 104 is adapted to extend into an aperture 150 that is formed in the moveable mechanism 108. The housing connector 104 is typically made of polymeric materials. One example of a polymeric material that may be used in forming the housing connector is polycarbonate. It is contemplated that other materials may be used in forming the housing connector.

Figure 7A:
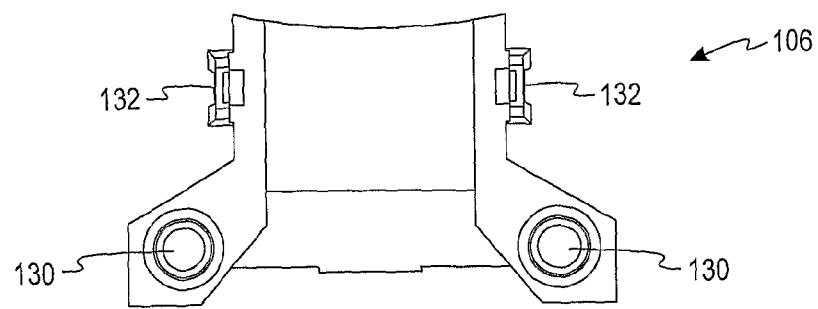
FIG. 7a is a top view of the base connector of FIG. 4.
Figure 7B:
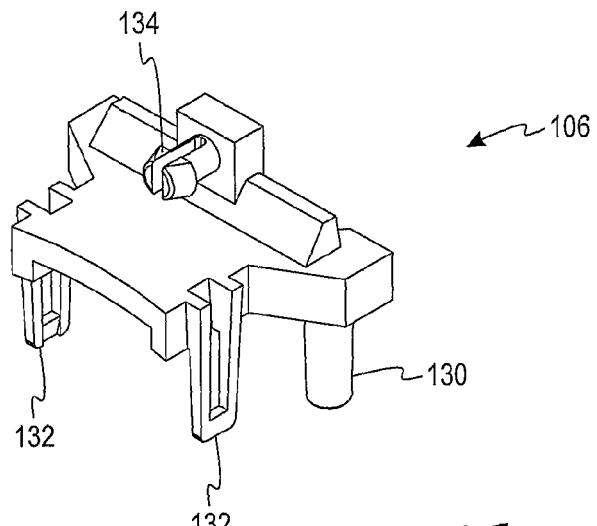
FIG. 7b is a top perspective view of the base connector of FIG. 4.
Figure 7C:
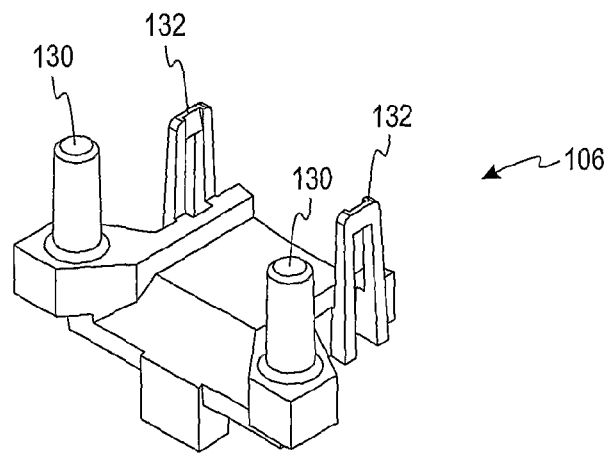
FIG. 7c is a bottom perspective view of the base connector of FIG. 4.

Referring to FIGS. 7*a-c*, the base connector 106 includes the plurality of posts 130, a plurality of generally rectangular-shaped legs 132, and a prong or extension 134. The posts 130 are adapted to extend into the apertures 114*a* that are formed in the housing connector 104. The number of posts 130 may vary from that depicted in FIGS. 7*a-c*. It is contemplated that the posts may be shaped different than depicted in FIGS. 7*a-c*.

Figure 6A:
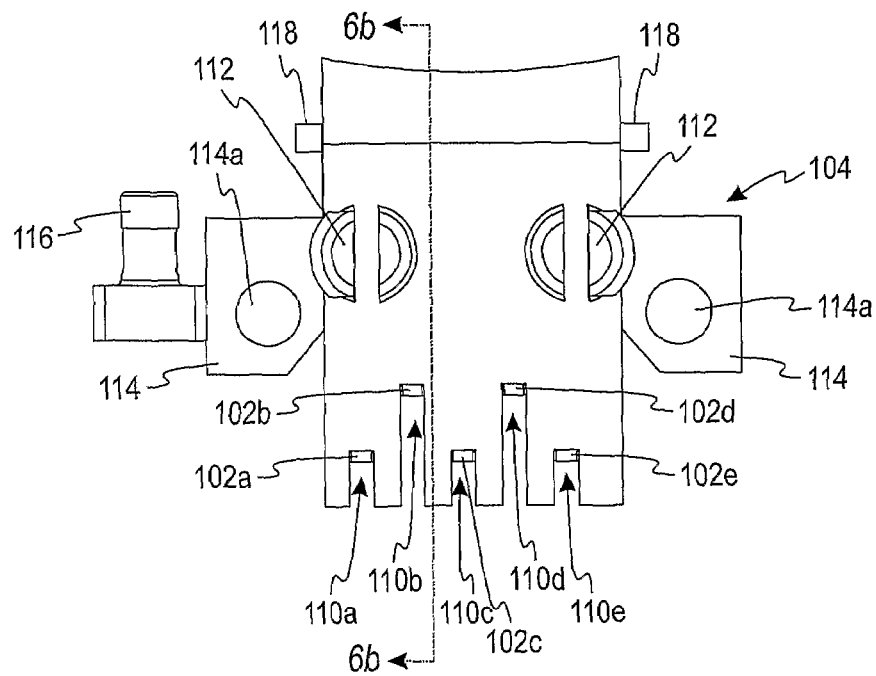
FIG. 6a is a top view of a housing connector with a plurality of electrical contacts of FIG. 4.
Figure 6B:
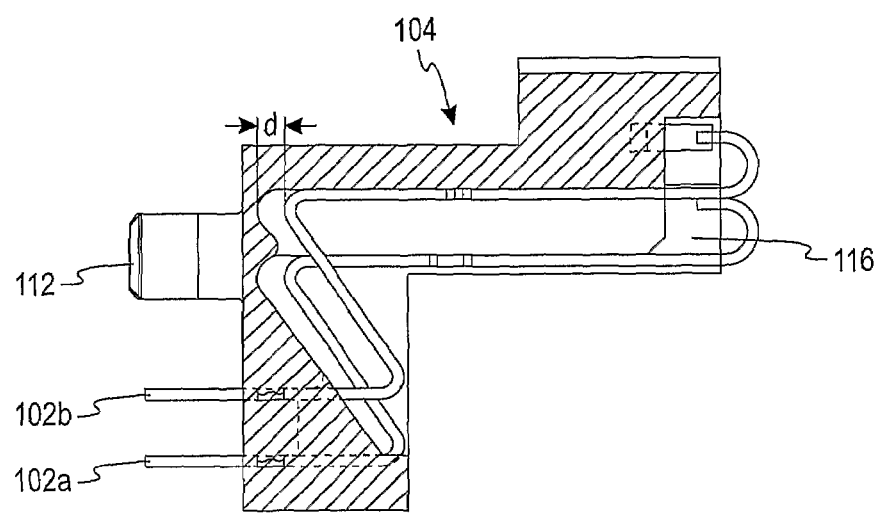
Figure 6C:
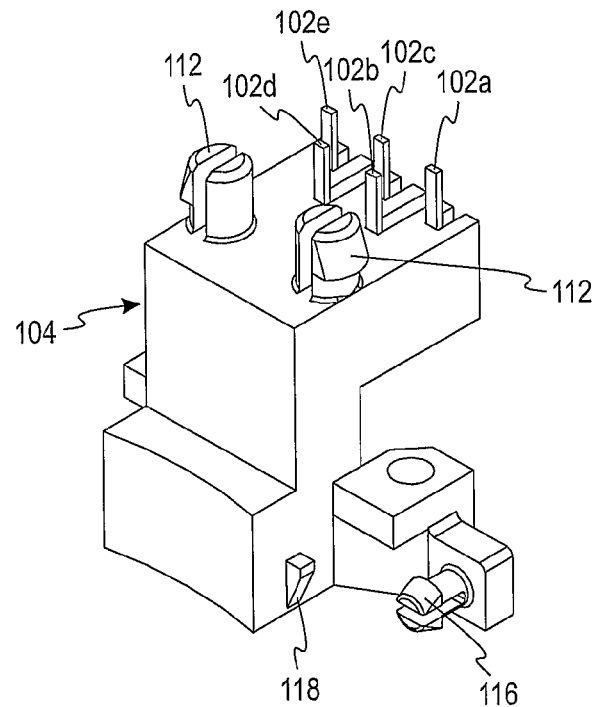
FIG. 6c, 6d are perspective views of the housing connector with a plurality of electrical contacts of FIG. 4.
Figure 6D:
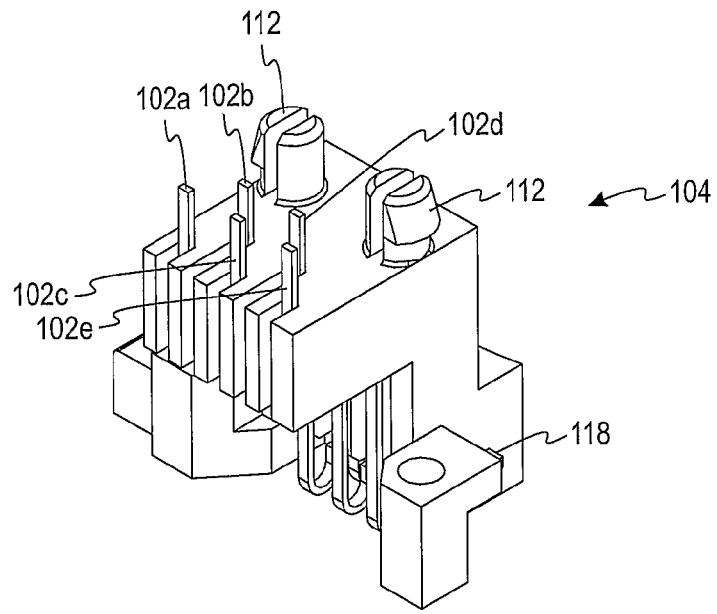

The generally rectangular-shaped legs 132 of FIGS. 7*a-c* are adapted to snap over a respective one of the plurality of generally triangular-shaped plugs 118 (see FIGS. 6*a, c, d*). The plugs 118 are designed to allow the base connector 106 to move from a first position to a second position, while still being coupled to the housing connector 104. The base connector 106 is coupled to the housing connector 104 as shown in FIGS. 5*a-d*.

The posts 130 and the plurality of legs 132 of the base connector 106 work with receiving portions 114 and the plurality of plugs 118 of the housing connector 104 to couple the base connector 106 and the housing connector 104. When the housing connector 104 and the base connector 106 are coupled together such as shown in FIGS. 5*a, b*, they form a sensor-receiving opening 140*a* that is adapted to receive one of the plurality of test sensors. The opening 140*a* has a floor 142 in which one of the plurality of test sensors may rest thereon.

As shown in FIG. 5*b*, the prong 134 of the base connector 106 is adapted to extend into an aperture 152 that is formed in the moveable mechanism 108. The prong 134 and the aperture 152 form a snap fit. It is contemplated that the base connector and the moveable mechanism may be attached by other methods.

The base connector 106 is adapted to move between a first position (FIGS. 5*a,b*) and a second position (FIGS. 5*c,d*). In the first position, a test sensor is held in place during the testing after being repositioned into the opening 140*a* from the cartridge. In one embodiment, the sensor-receiving opening 140*a* is sized such that the height of the opening 140*a* is roughly the same as the thickness of the test sensor. For example, the height of the opening 140*a* may be about 15 mils and the thickness of the test sensor may be about 15 mils. It is contemplated that the height of opening 140*a*, as well as the test sensor, may be of different dimensions.

After the testing has been completed, the used test sensor is removed. To remove the test sensor, the base connector 106 in one embodiment is moved to a second position by lowering the base connector 106 with respect to the housing connector 104. When the base connector 106 is moved to a second position, the opening begins larger (see opening 140*b* in FIGS. 5*c,d*) and the grip on the test sensor lessens. To assist in removing the test sensor, the opening 140*b* is sized such that the height of the opening 140*b* is greater than the thickness of the test sensor. For example, the height of the opening 140*b* may be about 30 mils and the thickness of the test sensor may be about 15 mils. It is contemplated that the height of the opening 140*b* may be of a different dimension.

By having a larger opening, the user may remove the test sensor by, for example, tipping the sensor-dispensing instrument such the test sensor exits via gravity. It is contemplated that the test sensor may be removed by other methods such as grasping and pulling the test sensor from the sensor-dispensing instrument. Alternatively, a button may be pressed that results in the test sensor being ejected from the sensor-dispensing instrument. It is also contemplated that the test sensor may be removed from the sensor-dispensing instrument by a pivoting lever or pulling mechanism.

According to another embodiment, the housing connector instead of the base connector may be adapted to move between a first position and a second position such as been described above with respect to the base connector. In such an embodiment, the moveable mechanism may be adapted to move the housing connector between the first and second positions.

To move the base connector 106 with respect to the housing connector 104, a moveable mechanism may be used such as moveable mechanism 108 shown in FIGS. 4, 5. The moveable mechanism 108 of FIGS. 4, 5 is a lever or pivoting arm. The moveable mechanism 108 moves the base connector 106 between the first position (FIGS. 5*a, b*) and the second position (see FIGS. 5*c,d*). To assist in maintaining the moveable mechanism in the first position, the moveable mechanism may include a spring or other suitable component.

The moveable mechanism is shown in FIGS. 5*a*-*d* as being connected both to the housing connector 104 and the base connector 106. It is contemplated, however, that the moveable mechanism may be connected to exactly one of the housing connector and the base connector. For example, the moveable mechanism may be connected only to the housing connector, but not the base connector. Similarly, the moveable mechanism may be connected only to the base connector, but not the housing connector. In such embodiments, either the housing connector or the base connector would need to be moved with respect to either other so as to form a sensor-receiving opening.

The moveable mechanism 108 is shown as moving the base connector with respect to the housing connector. It is contemplated that the moveable mechanism may be connected such that the housing connector may be moved with respect to the base connector. In such an embodiment, the housing connector instead of the base connector would be moved between first and second positions. Alternatively, both the housing and the base connector may be moved with respect to each other. In such an embodiment, both the housing connector and the base connector would be moved between respective first positions and respective second positions.

According to one method, a sensor-dispensing instrument is provided that is adapted to include a cartridge (e.g., cartridges 10, 50 of FIGS. 1 and 2*a*) that contains a plurality of electrochemical test sensors. The sensor-dispensing instrument is activated by a user, which results in a test sensor being at least partially removed from the cartridge and repositioned to contact a portion of the contact connector assembly. The electrical contacts touch respective conductive pads on the test sensor. After the electrical contacts touch respective conductive pads, electrical current is allowed to flow to the electronic PC board.

According to one method, the software in the sensor-dispensing instrument detects the electrical current and performs an auto-calibration program. After the auto-calibration program is completed, the test sensor is ready to accept a fluid for testing the concentration of at least one analyte (e.g., blood glucose). The fluid is placed on the test sensor and the software begins a countdown to displaying the analyte concentration in the fluid sample.

To remove the test sensor from the sensor-dispensing instrument, a moveable mechanism is employed. One type of moveable mechanism that may be used is a lever. The lever may be, for example, pressed or pulled by a user, which allows at least one of the base connector and the housing connector to move to a second position. By moving at least one of the base connector and the housing connector to a second position, a wider opening is formed between the base connector and housing connector that enables the test sensor to be removed from the sensor-dispensing instrument.

Alternative Embodiment A

A contact connector assembly adapted to be used in a sensor-dispensing instrument that contains a plurality of electrochemical test sensors, the contact connector assembly comprising:

at least four electrical contacts;

a housing connector forming at least one housing opening, the at least one housing opening being adapted to receive the at least four electrical contacts;

a base connector being coupled to the housing connector so as to form a sensor-receiving opening adapted to receive one of the plurality of test sensors, at least one of the base connector and the housing connector being adapted to move between a first position and a second position; and a moveable mechanism coupled to at least one of the housing connector and the base connector, the moveable mechanism being adapted to move at least one of the base connector or the housing connector between the first position and the second position, wherein the housing connector and the base connector are adapted to be coupled in a first position such they are adapted to hold one of the plurality of test sensors and the housing connector and the base connector are adapted to be coupled in a second position such that they allow the test sensor to be removed therefrom.

Alternative Embodiment B

The assembly of embodiment A wherein the housing connector forms at least four housing openings, each of the at least four housing openings is adapted to receive a respective one of the at least four electrical contacts.

Alternative Embodiment C

The assembly of embodiment B wherein the at least four housing openings are slots.

Alternative Embodiment D

The assembly of embodiment A wherein the housing connector comprises a plurality of bosses and a plurality of base-connecting receiving portions.

Alternative Embodiment E

The assembly of embodiment D wherein the housing connector further includes an extension and a plurality of plugs, each of the plurality of base-connecting receiving portions forms an aperture.

Alternative Embodiment F

The assembly of embodiment A wherein the moveable mechanism is coupled to the housing connector and the base connector.

Alternative Embodiment G

The assembly of embodiment A wherein the moveable mechanism is a lever.

Alternative Embodiment H

The assembly of embodiment A wherein the base connector is adapted to move between a first position and a second position, the moveable mechanism is adapted to move the base connector between the first position and the second position.

Alternative Embodiment I

The assembly of embodiment A wherein the base connector includes a plurality of posts, a plurality of legs, and a prong.

Alternative Embodiment J

The assembly of embodiment A wherein the housing connector includes a plurality of plugs, the base connector includes a plurality of legs, each of the plurality of legs is adapted to snap over a respective one of the plurality of plugs.

Alternative Embodiment K

A sensor-dispensing instrument adapted to determine an analyte concentration, the sensor-dispensing instrument comprising:
a plurality of electrochemical test sensors;
a cartridge containing the plurality of electrochemical test sensors; and
a contact connector assembly including at least four electrical contacts, a housing connector that forms at least one housing opening, a base connector being coupled to the housing connector so as to form a sensor-receiving opening adapted to receive one of the plurality of test sensors, and a moveable mechanism coupled to at least one of the housing connector and the base connector, the at least one housing opening being adapted to receive the at least four electrical contacts, at least one of base connector and the housing connector being adapted to move between a first position and a second position, the moveable mechanism being adapted to move at least one of the base connector and the housing connector between the first position and the second position,
wherein the housing connector and the base connector are adapted to be coupled in a first position such they are adapted to hold one of the plurality of test sensors and the one of the plurality of test sensors is adapted to contact the at least four electrical contacts to assist in determining the analyte concentration,
wherein the housing connector and the base connector are adapted to be coupled in a second position such that they allow the test sensor to be removed therefrom.

Alternative Embodiment L

The sensor-dispensing instrument of embodiment K wherein the housing connector forms at least four housing openings, each of the at least four housing openings is adapted to receive a respective one of the at least four electrical contacts.

Alternative Embodiment M

The sensor-dispensing instrument of embodiment K wherein the at least four housing openings are slots.

Alternative Embodiment N

The sensor-dispensing instrument of embodiment K wherein the housing connector comprises a plurality of bosses and a plurality of base-connecting receiving portions.

Alternative Embodiment O

The sensor-dispensing instrument of embodiment N wherein the housing connector further includes an extension and a plurality of plugs, each of the plurality of base-connecting receiving portions forms an aperture.

Alternative Embodiment P

The sensor-dispensing instrument of embodiment K wherein the moveable mechanism is coupled to the housing connector and the base connector.

Alternative Embodiment Q

The sensor-dispensing instrument of embodiment K wherein the moveable mechanism is a lever.

Alternative Embodiment R

The sensor-dispensing instrument of embodiment K wherein the base connector is adapted to move between a first position and a second position, the moveable mechanism is adapted to move the base connector between the first position and the second position, and wherein the base connector in the first position is adapted to hold one of the plurality of test sensors and the base connector in the second position is adapted to allow the test sensor to be removed therefrom.

Alternative Embodiment S

The sensor-dispensing instrument of embodiment K wherein the base connector includes a plurality of posts, a plurality of legs, and a prong.

Alternative Embodiment T

The sensor-dispensing instrument of embodiment K wherein the housing connector includes a plurality of plugs, the base connector includes a plurality of legs, each of the plurality of legs is adapted to snap over a respective one of the plurality of plugs.

Alternative Embodiment U

A method of using a sensor-dispensing instrument to determine an analyte concentration, the method comprising the acts of:
providing a sensor-dispensing instrument including a plurality of electrochemical test sensors, a cartridge containing the plurality of electrochemical test sensors and a contact connector assembly, the contact connector assembly including at least four electrical contacts, a housing connector that forms at least one housing opening, a base connector being coupled to the housing connector so as to form a sensor-receiving opening adapted to receive one of the plurality of test sensors, and a moveable mechanism coupled to at least one of the housing connector and the base connector, the at least one housing opening being adapted to receive the at least four electrical contacts, placing at least one of the base connector and the housing connector in a first position;

repositioning one of the plurality of test sensors from the cartridge to the sensor-receiving opening such that the one of the plurality of test sensors contacts the at least four electrical contacts to assist in determining the analyte concentration;

moving at least one of the base connector and the housing connector to a second position from the first position via the moveable mechanism;

placing a fluid with at least one analyte on the one of the plurality of test sensors; and determining the concentration of the at least one analyte.

Alternative Embodiment V

The method of embodiment U further including removing the one of the plurality of test sensors from the contact connector assembly when at least one of the base connector and the housing connector is in the second position.

Alternative Embodiment W

The method of embodiment U wherein the analyte is glucose.

Alternative Embodiment X

The method of embodiment U wherein the fluid is blood.

Alternative Embodiment Y

The method of embodiment U wherein the housing connector forms at least four housing openings, each of the at least four housing openings is adapted to receive a respective one of the at least four electrical contacts.

Alternative Embodiment Z

The method of embodiment U wherein the moveable mechanism is coupled to the housing connector and the base connector.

Alternative Embodiment AA

The method of embodiment U wherein the moving includes moving the base connector between a first position and a second position, the moveable mechanism is adapted to move the base connector between the first position and the second position.

The invention claimed is:

1. A contact connector assembly adapted to be used in a sensor-dispensing instrument that contains a plurality of electrochemical test sensors, the contact connector assembly comprising:

at least four electrical contacts;

a housing connector forming at least one housing opening, the at least one housing opening being adapted to receive the at least four electrical contacts;

a base connector being coupled to the housing connector so as to form a sensor-receiving opening adapted to receive one of the plurality of test sensors, at least one of the base connector and the housing connector being adapted to move between a first position and a second position; and a moveable mechanism coupled to at least one of the housing connector and the base connector, the moveable mechanism being adapted to move at least one of the base connector or the housing connector between the first position and the second position, wherein the housing connector and the base connector are adapted to be coupled in a first position such they are adapted to hold one of the plurality of test sensors and the housing connector and the base connector are adapted to be coupled in a second position such that they allow the test sensor to be removed therefrom.

2. The assembly of claim 1 wherein the housing connector forms at least four housing openings, each of the at least four housing openings is adapted to receive a respective one of the at least four electrical contacts.

3. The assembly of claim 2 wherein the at least four housing openings are slots.

4. The assembly of claim 1 wherein the housing connector comprises a plurality of bosses and a plurality of base-connecting receiving portions.

5. The assembly of claim 4 wherein the housing connector further includes an extension and a plurality of plugs, each of the plurality of base-connecting receiving portions forms an aperture.

6. The assembly of claim 1 wherein the moveable mechanism is coupled to the housing connector and the base connector.

7. The assembly of claim 1 wherein the moveable mechanism is a lever.

8. The assembly of claim 1 wherein the base connector is adapted to move between a first position and a second position, the moveable mechanism is adapted to move the base connector between the first position and the second position.

9. The assembly of claim 1 wherein the base connector includes a plurality of posts, a plurality of legs, and a prong.

10. The assembly of claim 1 wherein the housing connector includes a plurality of plugs, the base connector includes a plurality of legs, each of the plurality of legs is adapted to snap over a respective one of the plurality of plugs.

11. A sensor-dispensing instrument adapted to determine an analyte concentration, the sensor-dispensing instrument comprising:

a plurality of electrochemical test sensors;

a cartridge containing the plurality of electrochemical test sensors; and a contact connector assembly including at least four electrical contacts, a housing connector that forms at least one housing opening, a base connector being coupled to the housing connector so as to form a sensor-receiving opening adapted to receive one of the plurality of test sensors, and a moveable mechanism coupled to at least one of the housing connector and the base connector, the at least one housing opening being adapted to receive the at least four electrical contacts, at least one of base connector and the housing connector being adapted to move between a first position and a second position, the moveable mechanism being adapted to move at least one of the base connector and the housing connector between the first position and the second position, wherein the housing connector and the base connector are adapted to be coupled in a first position such they are adapted to hold one of the plurality of test sensors and the one of the plurality of test sensors is adapted to contact the at least four electrical contacts to assist in determining the analyte concentration,
wherein the housing connector and the base connector are adapted to be coupled in a second position such that they allow the test sensor to be removed therefrom.

12. The sensor-dispensing instrument of claim 11 wherein the housing connector forms at least four housing openings, each of the at least four housing openings is adapted to receive a respective one of the at least four electric contacts.

13. The sensor-dispensing instrument of claim 11 wherein the at least four housing openings are slots.

14. The sensor-dispensing instrument of claim 11 wherein the housing connector comprises a plurality of bosses and a plurality of base-connecting receiving portions.

15. The sensor-dispensing instrument of claim 14 wherein the housing connector further includes an extension and a plurality of plugs, each of the plurality of base-connecting receiving portions forms an aperture.

16. The sensor-dispensing instrument of claim 11 wherein the moveable mechanism is coupled to the housing connector and the base connector.

17. The sensor-dispensing instrument of claim 11 wherein the moveable mechanism is a lever.

18. The sensor-dispensing instrument of claim 11 wherein the base connector is adapted to move between a first position and a second position, the moveable mechanism is adapted to move the base connector between the first position and the second position, and wherein the base connector in the first position is adapted to hold one of the plurality of test sensors and the base connector in the second position is adapted to allow the test sensor to be removed therefrom.

19. The sensor-dispensing instrument of claim 11 wherein the base connector includes a plurality of posts, a plurality of legs, and a prong.

20. The sensor-dispensing instrument of claim 11 wherein the housing connector includes a plurality of plugs, the base connector includes a plurality of legs, each of the plurality of legs is adapted to snap over a respective one of the plurality of plugs.

21. A method of using a sensor-dispensing instrument to determine an analyte concentration, the method comprising the acts of:
providing a sensor-dispensing instrument including a plurality of electrochemical test sensors, a cartridge containing the plurality of electrochemical test sensors and a contact connector assembly, the contact connector assembly including at least four electrical contacts, a housing connector that forms at least one housing opening, a base connector being coupled to the housing connector so as to form a sensor-receiving opening adapted to receive one of the plurality of test sensors, and a moveable mechanism coupled to at least one of the housing connector and the base connector, the at least one housing opening being adapted to receive the at least four electrical contacts,
placing at least one of the base connector and the housing connector in a first position;
repositioning one of the plurality of test sensors from the cartridge to the sensor-receiving opening such that the one of the plurality of test sensors contacts the at least four electrical contacts to assist in determining the analyte concentration;
moving at least one of the base connector and the housing connector to a second position from the first position via the moveable mechanism;
placing a fluid with at least one analyte on the one of the plurality of test sensors; and
determining the concentration of the at least one analyte.

22. The method of claim 21 further including removing the one of the plurality of test sensors from the contact connector assembly when at least one of the base connector and the housing connector is in the second position.

23. The method of claim 21 wherein the analyte is glucose.

24. The method of claim 21 wherein the fluid is blood.

25. The method of claim 21 wherein the housing connector forms at least four housing openings, each of the at least four housing openings is adapted to receive a respective one of the at least four electrical contacts.

26. The method of claim 21 wherein the moveable mechanism is coupled to the housing connector and the base connector.

27. The method of claim 21 wherein the moving includes moving the base connector between a first position and a second position, the moveable mechanism is adapted to move the base connector between the first position and the second position.

* * * * *